United States Patent [19]

Thompson et al.

[11] Patent Number: 4,701,528
[45] Date of Patent: Oct. 20, 1987

[54] INTERMEDIATES USEFUL IN THE PREPARATION OF 3,4-DIHYDRO-4-OXOTHIENO[2,3-D]PYRIMIDINE-2-CARBOXYLATES AND PROCESS FOR PREPARING SAME

[75] Inventors: Michael D. Thompson; Gary D. Madding, both of Evansville, Ind.

[73] Assignee: Bristol-Myers Company, New York, N.Y.

[21] Appl. No.: 812,166

[22] Filed: Dec. 23, 1985

[51] Int. Cl.[4] .......................................... C07D 495/04
[52] U.S. Cl. .................................... 544/278; 544/250; 549/68
[58] Field of Search .......................... 544/278, 250

[56] References Cited

U.S. PATENT DOCUMENTS 4,054,656 10/1977 Temple, Jr. .................... 544/278
4,159,377 6/1979 Temple, Jr. .................... 544/278

OTHER PUBLICATIONS von Walter Ried and Roland Giesse, Liebigs Ann. Chem. 713, 143–148 (1968).
Temple, et al., *Journal of Medicinal Chemistry*, 1979, vol. 22, No. 5, pp. 505–510.
Gewald, et al., *Chem. Ber.*, 99, (1966), pp. 94–100.

*Primary Examiner*—Donald G. Daus
*Assistant Examiner*—Barbara Cassatt
*Attorney, Agent, or Firm*—Robert H. Uloth

[57] ABSTRACT

There are disclosed compounds of Formulas I and II:

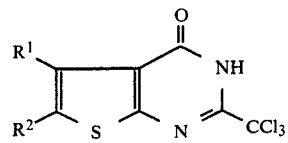

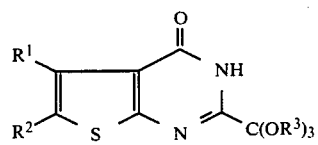

wherein $R^1$ and $R^2$ may be hydrogen, lower alkyl having from 1 to 8 carbon atoms, lower alkenyl having from 3 to 6 carbon atoms, lower alkoxy having from 1 to 6 carbon atoms, hydroxy, nitro, amino, halo including chlorine, bromine, iodine, and fluorine, phenyl, alkanoyl having from 2 to 6 carbon atoms or they are bonded to one another to form a cycloalkene ring fused to the thiophene ring and having a total of from 5 to 7 annular ring carbon atoms, and $R^3$ is an aliphatic or an aromatic group such as lower alkyl, e.g., methyl or ethyl. Such compounds are useful as intermediates in the production of tiprinast and related compounds.

There is also disclosed a process for the regioselective synthesis of a compound of Formula I wherein $R^1$ is $CH_3$ and $R^2$ is $(CH_3)_2CHCH_2$ which comprises reacting a mixture of compounds of the following formulas:

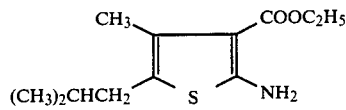

and

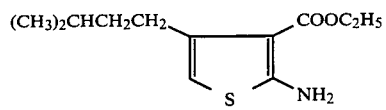

with trichloroacetonitrile under acidic conditions.

5 Claims, No Drawings

INTERMEDIATES USEFUL IN THE PREPARATION OF 3,4-DIHYDRO-4-OXOTHIENO[2,3-D]PYRIMIDINE-2-CARBOXYLATES AND PROCESS FOR PREPARING SAME

BACKGROUND OF THE INVENTION

This invention relates to novel intermediates useful in the preparation of 3,4-dihydro-5-methyl-6-(2-methylpropyl)-4-oxothieno[2,3-d]pyrimdine-]-carboxylic acid (tiprinast) and related compounds. This invention also relates to the regioselective synthesis of such intermediates.

Tiprinast, which has the formula

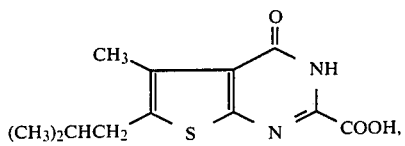

and related compounds are useful as orally active antiallergy agents. The preparation of tiprinast and related compounds is described in U.S. Pat. Nos. 4,054,656 and 4,159,377 to Davis L. Temple, Jr., the disclosures of which are incorporated herein by reference. Esters of tiprinast and related compounds, which are also useful as orally active antiallergy agents, are disclosed in an article by D. L. Temple et al, *J. Med. Chem.*, Volume 22, pages 505–510 (1979), the disclosure of which is incorporated herein by reference. The basic approach to these compounds has been to construct the pyrimidinone ring on a 2-amino-3-carboxy substituted thiophene, which in turn is available from procedures published by K. Gewald et al in *Chem. Ber.*, 99, pages 94–100 (1966). However, the Gewald et al procedures result in a mixture of 2-aminothiophene-3-carboxylate isomers which are not easily separated. The present invention permits the use of this mixture of isomers without separation.

SUMMARY OF THE INVENTION

This invention provides compounds of Formulas I and II:

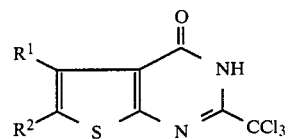

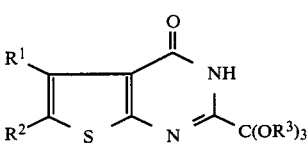

wherein $R^1$ and $R^2$ may be hydrogen, lower alkyl having from 1 to 8 carbon atoms, lower alkenyl having from 3 to 6 carbon atoms, lower alkoxy having from 1 to 6 carbo atoms, hydroxy, nitro, amino, halo including chlorine, bromine, iodine, and fluorine, phenyl, alkanoyl having from 2 to 6 carbon atoms or they are bonded to one another to form a cycloalkene ring fused to the thiophene ring and having a total of from 5 to 7 annular ring carbon atoms, and $R^3$ is an aliphatic group or an aromatic group such as lower alkyl, e.g., methyl or ethyl. Such compounds are useful as intermediates in the production of tiprinast and related compounds.

This invention also provides a process for the regioselective synthesis of a compound of Formula I wherein $R^1$ is $CH_3$ and $R^2$ is $(CH_3)_2CHCH_2$ which comprises reacting a mixture of compounds of the following formulas:

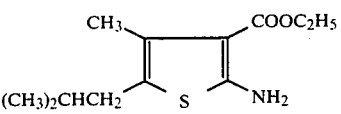

and

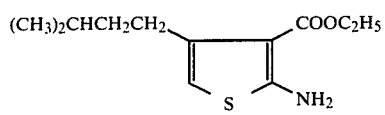

with trichloroacetonitrile under acidic conditions.

DETAILED DESCRIPTION OF THE INVENTION

The mixture of compounds of Formulas III and IV is prepared by the general procedure described by K. Gewald et al in *Chem. Ber.*, 99, pages 94–100 (1966), the disclosure of which is incorporated herein by reference. This mixture is reacted wih trichloroacetonitrile using anhydrous hydrochloric acid. Preferably, the reaction is conducted at a temperature ranging from room temperature to the reflux temperature of acetic acid for a period of from 2 hours to 24 hours. Preferably, from about 0.2 to 2.0 mol of trichloroacetonitrile is used per mol of the mixture of Compounds III and IV. There is thus obtained a compound of Formula I wherein $R^1$ is $CH_3$ and $R^2$ is $(CH_3)_2CHCH_2$. Surprisingly, the isolated trichloromethyl intermediate is free from the isomer which would be expected from reaction of Compound IV with trichloroacetonitrile, i.e., a compound of Formula I wherein $R^1$ is $(CH_3)_2CHCH_2CH_2$ and $R^2$ is hydrogen. If any of that isomer was present, it is lost during work-up.

The trichloromethyl intermediate, i.e., the compound of Formula I where $R^1$ is $CH_3$ and $R^2$ is $(CH_3)_2CHCH_2$, can be converted to the compound of Formula II wherein $R^1$ is $CH_3$, $R^2$ is $(CH_3)_2CHCH_2$ and $R^3$ is $CH_3CH_2$, by heating it at reflux with excess sodium ethoxide. Similarly, the corresponding compound where $R^3$ is methyl, may be obtained by heating the trichloromethyl intermediate at reflux with sodium methoxide. The triethers can then be converted to the ethyl or methyl ester of tiprinast by treatment with acid, e.g., 10% HCl.

Alternatively, rather than isolating the triether intermediate, i.e., compounds of Formula II, the trichloromethyl intermediate described above may be converted to the ethyl ester of tiprinast by refluxing it with excess sodium ethoxide and then immediately mixing it with acid, preferably dilute aqueous acid. Similarly, the methyl ester of tiprinast may be prepared by refluxing the trichloromethyl intermediate with sodium methoxide and then mixing it with acid, preferably dilute aqueous acid. The methyl and ethyl esters of tiprinast may be hydrolyzed under known conditions to give tiprinast.

The following examples illustrate the best modes contemplated for carrying out this invention. Melting points were determined using a Buchi 510 capillary melting point apparatus and are uncorrected. Infrared spectra were recorded on a Nicolet MX1 spectrophotometer. Proton magnetic resonance spectra were recorded on a Perkin-Elmer R32 instrument. Chemical shifts are reported as values in parts per million relative to tetramethylsilane as an internal standard (00.0). High performance liquid chromatography was done using an HP 1080n series chromatograph with a 25 μL injection loop, Varian Autosampler, 320 nanometers detection and an HP 1084 microprocessor. All temperatures are degrees Celsius.

EXAMPLE 1

Ethyl 2-Amino-4-methyl-5-(2-methylpropyl)thiophene-3-carboxylate and Ethyl-2-Amino-4-(3-methylbutyl)-thiophene-3-carboxylate (III and IV)

A mixture of 3140.3 g (27.5 mole) of 5-methyl-2-hexanone, 2828 g (25.0 mole) of ethyl cyanoacetate, 1927.1 g (25.0 mole) of ammonium acetate, 217.8 g (2.5 mole) of morpholine and 7.5 L of toluene was stirred and heated at reflux with a water-trap for 8 hours. The reaction mixture was washed with water (3×5 L) and the solvent was distilled in vacuo. Sulfur (761.5 g, 23.75 g-atom), 2530.0 g (25.0 mole) of triethylamine and 7.0 L of absolute ethanol were added to the oil, and the mixture was stirred and heated under reflux for 6 hours. The mixture was cooled and stirred with 10.0 L of cold water. The layers were separated, and the aqueous layer was extracted with methylene chloride (3×2 L). The combined organic layers were washed with water (2×2 L). The solution was filtered, and the filtrate was concentrated under reduced pressure to give 5222.0 g (91.1% theory) of dark oil which partially crystallized. This mixture of isomers was used without purification.

EXAMPLE 2

3,4-Dihydro-5-methyl-6-(2-methylpropyl)-4-oxo-2-(trichloromethyl)thieno[2,3-d]pyrimidine (I wherein $R^1$ is $CH_3$ and $R^2$ is $(CH_3)_2CHCH_2$)

Gaseous hydrochloric acid (1.45 mol) was bubbled into 437.5 ml (7.6 mole) of glacial acetic acid at 10° (±2°). After 30 minutes the bubbling was stopped, and nitrogen was swept across the solution for 30 minutes at 10° (±2°). This solution was added to a mixture of 350.0 g (4.55 mole) of the mixture of isomers obtained in Example 1 and 291.2 ml (2.02 mole) of trichloroacetonitrile in 350 ml of acetic acid. The resulting mixture was heated with stirring on a steam bath overnight. The solvent was removed under reduced pressure and 1 liter of isopropanol was added. This mixture was warmed on a steam bath to reflux and then was cooled to room temperature with stirring. After cooling in a refrigerator overnight, the mixture was filtered and rinsed with cold isopropanol giving a tan solid, which when dry, weighed 198.0 g (0.58 mole, 40% yield); mp 189°–192°. This was used without further purification. An analytical sample of the title compound was prepared by successive recrystallization with acetone (1:35), toluene (1:6), and isopropanol (1:30) giving white crystals; mp 192°–193.5°; ir (0.5%) potassium bromide) 3400 (br), 2960, 2875, 1675(s), 1580, 1470, 1310, 1210, 850, 780 and 675 cm$^{-1}$; nmr (deuteriochloroform): δ 0.85 (d, CH(CH$_3$)$_2$, 6H, J=6 Hz), 1.8 (m, CH, 1H), 2.45 (s, ArCH$_3$, 3H), 2.65 (d, ArCH$_2$, 3H, J=6 Hz), and 12.6 (s, NH, 1H).

Anal. Calcd. for $C_{12}H_{13}Cl_3N_2OS$: C, 42.43; H, 3.86; N, 8.25; S, 9.44; Cl, 31.31. Found: C, 42.45; H, 3.81; N, 8.36; S, 9.56; Cl, 31.16.

EXAMPLE 3

3,4-Dihydro-5-methyl-6-(2-methylpropyl)-4-oxo-2-(triethoxymethyl)thieno]2,3-d]pyrimidine (II wherein $R^1$ is $CH_3$, $R^2$ is $(CH_3)_2CHCH_2$ and $R^3$ is $C_2H_5$)

To a mixture of sodium ethoxide in ethanol, generated from 1.0 g (43 mmole) of sodium in 200 ml of ethanol, a mixture of 3.0 g (8.8 mmole) of the trichloromethyl intermediate obtained in Example 2 in 50 ml of toluene was added. This was heated to reflux for 18 hours. After cooling and solvent removal under reduced pressure, the residue was taken up in 25 ml of ethanol and poured into 50 ml of 5% aqueous sodium bicarbonate solution. This was extracted with 3×25 ml of toluene. The combined organic layer was dried with anhydrous magnesium sulfate and filtered. The solvent was removed under reduced pressure and the remaining solid, which was the title compound, was recrystallized with absolute ethanol (1:5) giving 1.2 g (3.2 mmole, 36% yield) of white needles; mp 135.5°–137°; ir (0.5% potassium bromide) 3400 (br), 3175, 3100, 2995, 1660, 1270, 1210, 1140, 1125, 1080, 1000, and 900 cm$^{-1}$; nmr (deuteriochloroform): δ 1.00 (d, CH(CH$_3$)$_2$, 6H, J=6 Hz) 1.33 (s, OCH$_2$CH$_3$), 9H, J=6 Hz) 1.9 (m, CH, 1H) 2.56 (s, ArCH$_3$, 3H) 2.71 (d, ArCH$_2$, 2H, J=6 Hz), 3.67 (q, OCH$_2$, 6H, J=6 Hz) 9.8 (s, NH, 1H).

Anal. calcd. for: C, 58.67; H, 7.66; N, 7.60; S, 8.70. Found: C, 58.85; H, 7.81; N, 7.75; S, 8.74. The product can be converted to the ethyl ester of tiprinast by treatment with 10% HCl.

EXAMPLE 4

3,4-Dihydro-5-methyl-6-(2-methylpropyl)-4-oxo-2-(trimethoxymethyl)thieno[2,3-d]pyrimidine (II wherein $R^1$ is $CH_3$, $R^2$ is $(CH_3)_2CHCH_2$ and $R^3$ is $CH_3$)

To a mixture of sodium methoxide in methanol, generated from 12.8 g (0.56 mole) of sodium in 250 ml of methanol, 34.0 g (0.10 mole) of the trichloromethyl intermediate obtained in Example 2 was added. This was heated to reflux for two hours. After cooling, the mixture was poured into 250 ml of 5% aqueous sodium bicarbonate solution and extracted with 3×100 ml of methylene chloride. The combined organic layer was dried with anhydrous magnesium sulfate and filtered. The solvent was removed under reduced pressure and the remaining solid, which was the title compound, was recrystallized with methanol giving 11.1 g (0.034 mole, 34% yield) of white crystals; mp 152°–154°; ir (0.5% potassium bromide) 3440 (br), 3110, 2950, 1650, 1575, 1490, 1460, 1440, 1270, 1205, 1100 and 990 cm$^{-1}$; nmr (deuteriochloroform): δ 1.00 (d, CH(CH$_3$)$_2$, 6H, J=7 Hz), 1.66 (s, ArCH$_3$, 3H), 1.78 (d, ArCH$_2$, 2H, J=7 Hz), 1.94 (m, CH, 1H), 3.52 (s, OCH$_3$, 9H), and 10.87 (brs, NH, 1H).

Anal. Calcd. for: C, 55.20; H, 2.79; N, 8.58. Found: C, 55.15; H, 6.70; N, 8.54. The product can be converted to the methyl ester of tiprinast by treatment with 10% HCl.

Examples 5 and 6 illustrate the preparation of the ethyl ester of tiprinast and the methyl ester of tiprinast, respectively, from the trichloromethyl intermediate of Example 2 without isolating the products obtained in Examples 3 and 4.

EXAMPLE 5

Ethyl 3,4-Dihyddro-5-methyl-6-(2-methylpropyl)-4-oxothieno-[2,3-d]pyrimidine-2-carboxylate (ethyl ester of tiprinast)

To a solution of sodium ethoxide in ethanol, generated from 95 g (4.0 mole) of sodium and 1500 ml of ethanol, 275 g (0.81 mole) of the trichloromethyl intermediate obtained in Example 2 was added. This mixture was heated to reflux eight hours. After cooling, the mixture was filtered. The dark solution was stirred wih one liter of water while 250 ml of 10% aqueous hydrochloric acid solution was added. The pH was acidic to litmus. After one hour of stirring at room temperature, this mixture was filtered and dried, giving 150 g of tan solid. Recrystallization with toluene (1:5) gave 122 g (0.415 mol, 51% yield) of off-white solid which was the title compound, mp 175.5°–177°; sepctral data was consistent with an authentic sample of the ethyl ester of tiprinast.

EXAMPLE 6

Methyl 3,4-Dihydro-5-methyl-6-(2-methylpropyl)-4-oxothieno-[2,3-d]pyrimidine-2-carboxylate (methyl ester of tiprinast)

To a solution of sodium methoxide in methanol, generated from 9 g (0.39 mole) of sodium and 125 ml of methanol 15.0 g (0.0442 mole) of the trichloromethyl intermediate obtained in Example 2 was added. This mixture was heated to reflux for two hours. After cooling, the mixture was filtered and rinsed with 200 ml of methanol. The resulting solution was stirred with 325 ml of water, then 75 ml of 10% hydrochloric acid solution was added. The pH was acidic to litmus. This was warmed with stirring to 50°, then cooled to 0°. Filtration followed by recrystallization with toluene (1:5) gave 8.3 g (0.030 mole, 67% yield) of white solid which was the title compound; mp 173°–175°; ir (0.5% potassium bromide) 3440 (br), 3090, 3040, 2950, 1740, 1670, 1560, 1490, 1460, 1440, 1300, 1200, and 1050 cm$^{-1}$; nmr (deuteriochloroform): δ 0.75 (d, CH(C$\underline{H}$$_3$), 6H, J=7 Hz), 1.75 (m, C$\underline{H}$, 1H), 2.50 (s, ArC$\underline{H}$$_3$, 3H), 2.56 (d, ArC$\underline{H}$$_2$, 2H, J=$\overline{7}$ Hz), 4.0 (s, OC$\underline{H}$$_3$, 3H), and 10.2 (brs, N$\underline{H}$, 1H).

Anal. Calcd. for: C, 55.70; H, 5.57; N, 9.99. Found: C, 55.74; H, 5.82; N, 10.07.

What is claimed is:

1. A compound having the formula

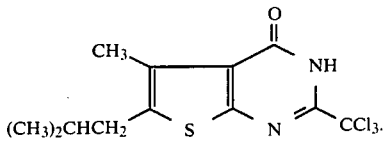

2. A compound having the formula:

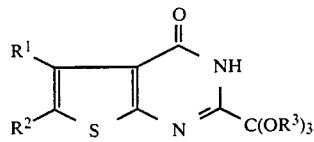

wherein $R^1$ and $R^2$ are selected from the group consisting of hydrogen, lower alkyl having from 1 to 8 carbon atoms, lower alkenyl having from 3 to 6 carbon atoms, lower alkoxy having from 1 to 6 carbon atoms, hydroxy, nitro, amino, halo, phenyl, alkanoyl having from 2 to 6 carbon atoms or they are bonded to one another to form a cycloalkene ring fused to the thiophene ring and having a total of from 5 to 7 annular ring carbon atoms, and $R^3$ is lower alkyl.

3. A compound as defined in claim 2 wherein $R^1$ is $CH_3$ and $R^2$ is $(CH_3)_2CHCH_2$.

4. A compound as defined in claim 3 wherein $R^3$ is ethyl.

5. A compound as defined in claim 3 wherein $R^3$ is methyl.

* * * * *